US00PP12786P2

(12) United States Plant Patent
Snow

(10) Patent No.: US PP12,786 P2
(45) Date of Patent: Jul. 23, 2002

(54) BEGONIA PLANT NAMED '77WL PEACH'

(75) Inventor: Andrew B. Snow, Aptos, CA (US)

(73) Assignee: Golden State Bulb Growers, Moss Landing, CA (US)

( * ) Notice: Subject to any disclaimer, the term of this patent is extended or adjusted under 35 U.S.C. 154(b) by 0 days.

(21) Appl. No.: 09/488,828

(22) Filed: Jan. 21, 2000

(51) Int. Cl.[7] ..... A01H 5/00
(52) U.S. Cl. ..... Plt./344
(58) Field of Search ..... Plt./344, 348

*Primary Examiner*—Bruce R. Campell
*Assistant Examiner*—Wendy C. Baker

(74) *Attorney, Agent, or Firm*—Richard C. Peet

(57) ABSTRACT

A new and distinct cultivar of Begonia plant named '77WL Peach', characterized by having a definite and distinct flower fragrance that can be described as sweet and lingering but subtle and not overpowering. It is often compared to the scent of a fragrant rose bloom. The fragrance is most pronounced when the temperature is between 65° and 80° F. The cultivar has a peach-color flower which is somtimes streaked with yellow. Male flowers are fully double and rarely produce pollen or male reproductive parts under normal growing conditions. '77WL Peach' has a full and semi-pendulous plant habit with numerous flower shoots (4–6 or more). Each flowering shoot will produce anywhere from 4–6 peduncles with 1 or 2 male flowers on each during the growing season.

2 Drawing Sheets

BACKGROUND OF THE INVENTION

The present invention relates to a new and distinctive cultivar of Begonia plant, botanically known as *Begonia tuberhybrida* (Pendula-type), and known by the cultivar name '77WL'Peach.

The new cultivar is a product of a planned breeding program and was originated from a hybridization made during such a program in Watsonville, Calif. in 1995. The female or seed parent was a proprietary Begonia selection designated 77FW-2389. The male or pollen parent was a proprietary Begonia selection designated 77KE-4063. '77WL Peach' was discovered and selected within the progeny of the stated cross by the inventor, Andrew B. Snow, in a controlled environment in Watsonville, Calif. in 1996.

The first act of asexual reproduction of '77WL Peach ' was accomplished by leaf and stem cuttings in 1997 in a controlled environment in Moss Landing, Calif. by Andrew B. Snow. Horticultural examination of selected units has demonstrated that the combination of characteristics as herein disclosed for '77WL Peach' are firmly fixed and are retained through successive generations of asexual reproduction.

BRIEF DESCRIPTION OF THE INVENTION

The following characteristics distinguish the new cultivar from both its parents and other Begonia cultivars commercially known and used in the floriculture industry:

1. a definite and distinct flower fragrance that can be described as sweet and lingering but subtle and not overpowering. It is often compared to the scent of a fragrant rose bloom. The fragrance is most pronounced when the temperature is between 65° and 80° F.;

2. peach-color flower which is sometimes streaked with yellow;

3. male flowers which are fully double and rarely produce pollen or male reproductive parts under normal growing conditions; and 4. full and semi-pendulous plant habit with numerous flower shoots (4–6 or more). Each flowering shoot will produce anywhere from 4–6 peduncles with 1 or 2 male flowers on each during the growing season.

'77WL Peach' has not been observed under all possible environmental conditions. The phenotype of the new cultivar may vary significantly with variations in environment such as temperature, light intensity, and daylength without any change in genotype.

Of the many commercial cultivars known to the present inventor, there is no known Begonia cultivar with which the new cultivar can be meaningfully compared. The color variance and gradation is unique, as is the distinct fragrance.

BRIEF DESCRIPTION OF THE DRAWINGS

The accompanying color photographic illustrations were taken on Aug. 20, 1999, and show typical flower and foliage characteristics of '77WL Peach' when grown in a 10-inch plastic pot, with colors being as true as possible with illustrations of this type.

The first drawing is a side elevational view of '77WL Peach'.

The second drawing is a top view of the claimed cultivar showing characteristics of the upper and lower surfaces of the flower and foliage.

DETAILED BOTANICAL DESCRIPTION

The following observations, measurements, and values describe a 2 year old tuber of '77WL Peach' as grown in Watsonville, Calif. under conditions which approximate those generally used in commercial practice. The plant is grown in a greenhouse with ambient temperatures of 60–75° F. The greenhouse is provided with a 50% shade cover that limits the light to under 2000 foot-candles. '77KK Blush Pink' is grown in a soiless mix and fed with a regular, complete fertilizer such as 20-10-20 at a rate of 200 ppm N, once every week.

Color references are made to The Royal Horticultural Society (R.H.S.) Colour Chart except where general terms of ordinary dictionary significance are used.

Classification:

*Botanical.*—A hybrid of the genus *Begonia tuberhybrida* (Pendula-type).

*Commercial.*—Begonia cv. 77WL Peach.

Parentage:

*Male parent.*—Begonia cultivar designated 77KE-4063.

*Female parent.*—Begonia cultivar designated 77FW-2389.

Propagation:

*Type cutting.*—Leaf and stem cuttings.

*Time to root.*—Approximately 24 to 30 days at 21° C. (summer) and 32 to 38 days at 21° C. (winter).

*Rooting habit/description.*—Abundant, fibrous and dendritic.

*Time for shoot development.*—Slow, 10 to 14 weeks in summer and up to 16 weeks in winter.

Plant:

*Form.*—Low mounding, semi-pendulous and herbaceous.

*Growth habit.*—Slow, uniform growth with numerous shoots and moderate branching habit at full growth. The plant is well rounded with a height of about 10 to 15 inches, excluding the container, with up to 20-inch pendulous shoots. The width is approximately 24 inches.

*Vigor.*—'77WL' makes a full vigorous plant approximately 12 weeks after planting a tuber, which has been given a sufficient dormant period, under growing conditions as previously described.

*Stem.*—RHS 46 A, with traces of green RHS 152 D.

Foliage:

*Habit.*—Simple, alternate, and borne on semi-rigid petioles 3 to 6 inches in length.

*Size.*—At maturity, the leaves reach 9 to 10 inches from base to apex, and at their widest point the leaves are 5.5 to 7 inches in width.

*Shape.*—Triangular-cordate with acuminate tip between rounded-based lobes.

*Texture.*—Firm, crisp, but not brittle; sparsely hirtellous on both surfaces.

*Margin.*—Doubly serrate.

*Color.*—Immature: Top surface: RHS 137A. Under surface: RHS 46A with veins colored RHS 142B. Mature: Top surface: RHS 147A. Under surface: RHS 46 A with veins, RHS 144 D, wider than immature foliage.

*Venation.*—Reticulate.

Flower:

*Habit.*—Flowering is presented on a pendulous raceme. Often, but not always, secondary male and female flowers will develop below the primary male and female flowers. Some peduncles have a solitary male flower, while others may have a solitary male flower accompanied by either a solitary secondary male flower or matching female flower and occasionally a secondary male and female flower.

*Natural flowering season.*—Summer and fall months.

*Lastingness of the individual bloom.*—It takes approximately 5–6 weeks for pollinated female flowers to ripen; individual blooms fade and the petals wither.

*Size.*—Male: Approximately 3.5 to 5 inches in diameter. Female: Approximately 2.5 to 3 inches in diameter.

*Buds.*—Flat, nearly round, tending towards bell shaped, approximately 4 cm long and 4 cm wide when opening, RHS 39 A.

*Borne.*—On small pedicels originating from long (5 to 8 inches) axillary peduncles, resulting in a solitary male flower, a solitary male and one or two female flowers, and occasionally secondary male and female flowers as raceme develops.

*Quantiy.*—Approximately 2 to 5 flowers per peduncle and numerous (3 to 5) peduncles per shoot, with 5 to 7 shoots per plant.

*Peduncle.*—Red, RHS 46 A where exposed to light and where it attaches to the stem, and green RHS 152 D where it is in deep shade.

Sepals:

*Number of sepals.*—2.

*Size of sepals.*—5–6 cm long, 6 cm wide.

*Shape of sepals.*—Orbicular, with slightly dentate margins.

Tepals:

*Shape.*—Round to obovate with a very slight ornate edge.

*Color.*—Top surface: In spring and summer when opening, RHS 48B to 48C with yellow-orange, RHS 15A, at attachment; some tepals with streaks of yellow-orange. Under surface: RHS 43A.

*Number.*—Approximately 45 to 55 on male flowers and 5 on female flowers.

*Size.*—Outer (male) up to 1.25 to 2 inches long and 1 to 2 inches wide.

Reproductive organs:

*Stamens.*—Petaloid, sometimes showing an occasional yellow anther, RHS 15A.

*Pistils.*—Stigma shape: Multi-lobed. Style color: Darker than RHS 12A but lighter than RHS 13A. Ovaries: Number: 3. Size: Approximately ½–⅝ inches. Color: RHS 144C with RHS 42B on tips if grown in high light. Fruit/seeds: No observations made.

Resistance to disease: Goods resistance to powdery mildrew, other fungus, and to *Xanthomas* bacteria blight.

I claim:

1. A new and distinct cultivar of Begonia plant named '77WL Peach', as illustrated and described.

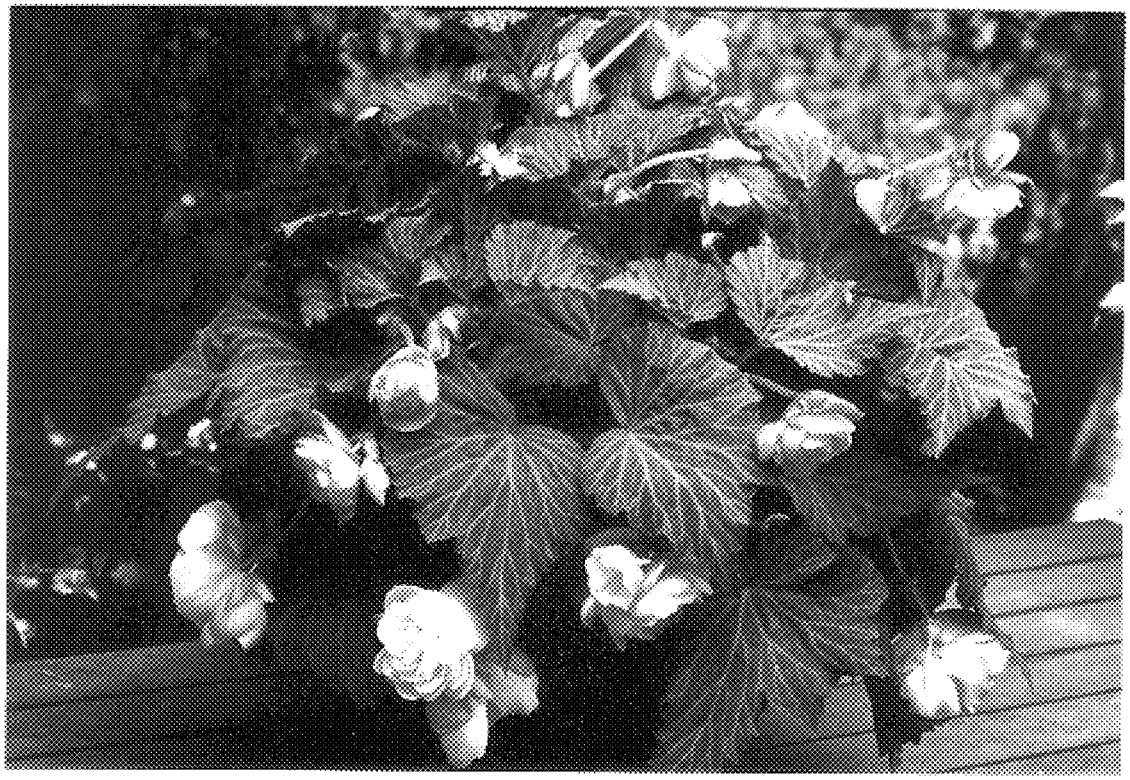

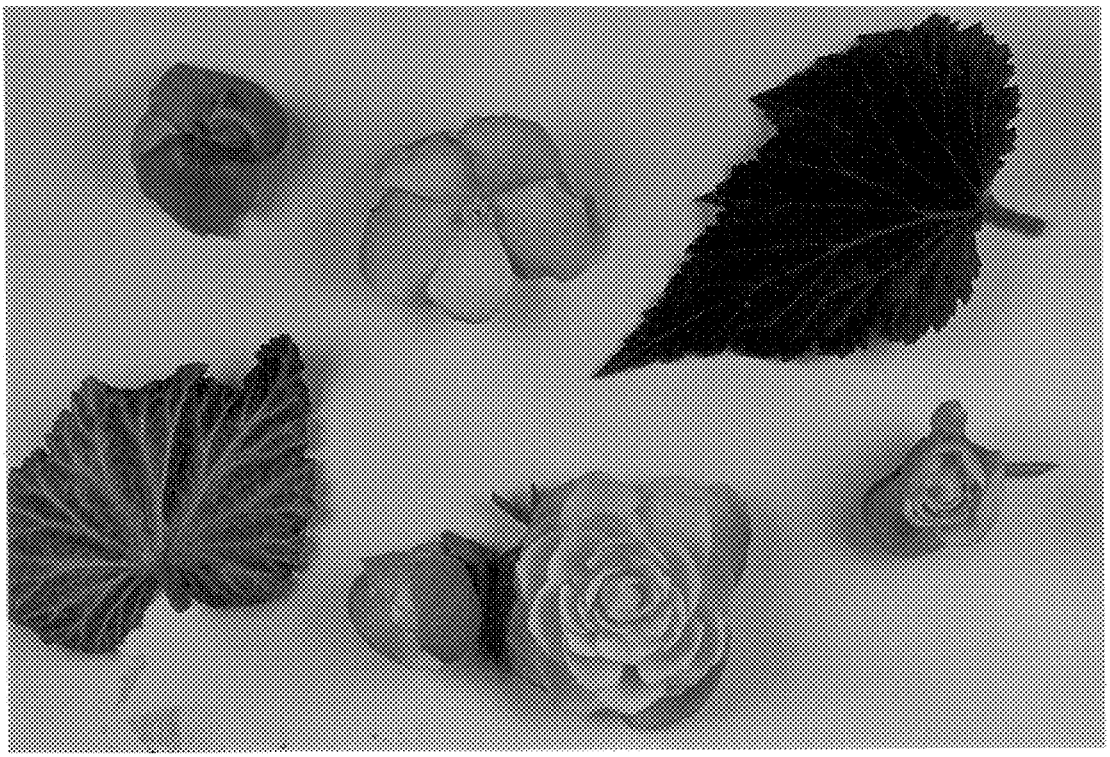

* * * * *